US009291541B2

(12) United States Patent
Kim et al.

(10) Patent No.: US 9,291,541 B2
(45) Date of Patent: Mar. 22, 2016

(54) APPARATUS AND METHOD OF MEASURING POROSITY AND PERMEABILITY OF DIOXIDE CARBON UNDERGROUND STORAGE MEDIUM

(71) Applicant: KOREA INSTITUTE OF GEOSCIENCE AND MINERAL RESOURCES, Daejeon (KR)

(72) Inventors: Kue-Young Kim, Daejeon (KR); Jun-Ho Oh, Daejeon (KR); Tae-Hee Kim, Daejeon (KR)

(73) Assignee: Korea Institute of Geoscience and Mineral Resources, Daejeon (KR)

( * ) Notice: Subject to any disclaimer, the term of this patent is extended or adjusted under 35 U.S.C. 154(b) by 629 days.

(21) Appl. No.: 13/657,766

(22) Filed: Oct. 22, 2012

(65) Prior Publication Data
US 2013/0144533 A1 Jun. 6, 2013

(30) Foreign Application Priority Data
Dec. 5, 2011 (KR) .......................... 10-2011-0129247

(51) Int. Cl.
*G01N 15/08* (2006.01)
(52) U.S. Cl.
CPC .......... *G01N 15/0806* (2013.01); *G01N 15/088* (2013.01); *G01N 15/0826* (2013.01)
(58) Field of Classification Search
CPC .............. G01N 15/0826; G01N 15/08; G01N 15/0813; G01N 15/0806; G01N 33/24; E21B 49/00; A61M 1/00
USPC ......... 73/38, 152.05, 152.07, 152.11, 152.41; 166/250.02, 252.1, 252.5; 702/1, 12, 702/50, 24, 138
See application file for complete search history.

(56) References Cited

U.S. PATENT DOCUMENTS

| | | | |
|---|---|---|---|
| 5,832,409 A * | 11/1998 | Ramakrishnan et al. | 702/12 |
| 7,082,812 B2 * | 8/2006 | Lenormand et al. | 73/38 |
| 7,229,593 B1 * | 6/2007 | Ho | G01N 13/00 422/50 |
| 2004/0211252 A1 * | 10/2004 | Lenormand et al. | 73/152.05 |
| 2005/0051327 A1 * | 3/2005 | Vinegar et al. | 166/256 |
| 2005/0178189 A1 * | 8/2005 | Lenormand et al. | 73/38 |
| 2008/0216559 A1 * | 9/2008 | Hilab | 73/38 |
| 2009/0211447 A1 * | 8/2009 | Lichtfers et al. | 95/201 |

(Continued)

FOREIGN PATENT DOCUMENTS

| | | |
|---|---|---|
| JP | 8-178827 A | 7/1996 |
| JP | 2007-64731 A | 3/2007 |

(Continued)

*Primary Examiner* — Toan Le
*Assistant Examiner* — Jeffrey Aiello
(74) *Attorney, Agent, or Firm* — Lewis Roca Rothgerber Christie LLP (57) ABSTRACT

Disclosed are an apparatus and a method of measuring porosity and permeability of a carbon dioxide underground storage medium. Both of the porosity and the permeability are measured in the state that the confining pressure is applied once. The variation characteristic in the porosity and the permeability of the core sample according to the salt precipitation occurring when supercritical carbon dioxide is injected is continuously measured. The apparatus includes a holder receiving a core sample, a pressure pump applying a confining pressure to the core sample, a gas chamber storing gas and supplying supply the stored gas to the core sample, first to third pressure gauges measuring an internal pressure of the gas chamber and front and rear portions of the holder, and a gas flow meter measuring a flow rate of gas.

14 Claims, 4 Drawing Sheets

(56) References Cited

U.S. PATENT DOCUMENTS

2010/0161229 A1\* 6/2010 Georgi et al. ................ 702/11
2011/0013986 A1\* 1/2011 Zebrowski .................... 405/53
2011/0056373 A1\* 3/2011 Baxter ........................... 95/213

FOREIGN PATENT DOCUMENTS

| KR | 2003-0077055 | 10/2003 |
|---|---|---|
| KR | 10-0642304 B1 | 11/2006 |
| KR | 10-2011-0044417 A | 4/2011 |

\* cited by examiner

APPARATUS AND METHOD OF MEASURING POROSITY AND PERMEABILITY OF DIOXIDE CARBON UNDERGROUND STORAGE MEDIUM

CROSS-REFERENCE TO RELATED APPLICATION

This application claims the benefit under 35 U.S.C. §119 of Korean Patent Application No. 10-2011-0129247 filed on Dec. 5, 2011 in the Korean Intellectual Property Office, the entirety of which disclosure is incorporated herein by reference.

BACKGROUND OF THE INVENTION

1. Field of the Invention

The present invention relates to a technology of analyzing the storage capacity of a land for the underground storage of carbon dioxide and the injection characteristic of the land for the underground storage of the carbon dioxide. In more detail, the present invention relates to a method and an apparatus for measuring porosity and permeability of a carbon dioxide underground storage medium, capable of measuring the porosity and the permeability of the carbon dioxide underground storage medium by using one device, and continuously measuring the variation characteristic in the porosity and the permeability of the carbon dioxide underground storage medium according to salt precipitation.

2. Description of the Related Art

When storing carbon dioxide ($CO_2$) under the ground, the porosity and the permeability of a storage medium reflecting the storage capacity and the injection characteristic of the land must be measured.

In general, the porosity and the permeability of a carbon dioxide underground storage medium are measured through an indoor experiment for the core sample acquired from a stratum in which the carbon dioxide is stored.

According to the related art, the porosity and the permeability of the core sample are separately measured by using different devices. In other words, according to the related art, after putting a core sample acquired from the stratum is into a holder for a porosity measuring device and introducing the holder into the porosity measuring device, the porosity of the core sample is measured in the state that a confining pressure is applied to the holder in order to realize an underground environment. If the porosity of the core sample has been finished, the confining pressure of the holder is released and the core sample is drawn from the holder. Then, after putting the core sample into a holder for a permeability measuring apparatus and introducing the holder into the permeability measuring apparatus, the permeability of the core sample is measured in the state that a confining pressure is applied to the holder in order to realize an underground environment.

As described above, according to the related art, since the porosity and the permeability of the core sample are separately measured, the device cost and the required time are increased. In particular, according to the related art, since the procedure of applying and releasing the confining pressure is repeatedly performed with respect to the same core sample, the core sample is denaturalized, so that the characteristic value of the core sample cannot be obtained.

Meanwhile, when supercritical carbon dioxide is stored under the ground, salt, which has been precipitated in the pores of the carbon dioxide underground storage medium, must be considered.

In general, salt water exists in the pores of the carbon dioxide underground storage medium. In this case, water of the salt water is evaporated due to the supercritical carbon dioxide, so that the salt is precipitated. The precipitated salt is filled in the pores of the underground storage medium, so that the porosity and the permeability are reduced. In other words, the porosity and the permeability coefficient of the underground storage medium are varied according to the injection time or the injected amount of the supercritical carbon dioxide.

Although the variation characteristic in the porosity and the permeability serves as an important factor in estimating a carbon dioxide underground storage land, the porosity measuring device or the permeability measuring device according to the related art cannot measure the continuous variation of the porosity and the permeability coefficient according to the salt precipitation.

The related art of the present invention includes Korean Unexamined Patent Publication No. 10-2003-0077055 (published in Oct. 1, 2003).

SUMMARY OF THE INVENTION

Accordingly, the present invention has been made keeping in mind the above problems occurring in the prior art, and an object of the present invention is to provide an apparatus for measuring porosity and permeability of a carbon dioxide underground storage medium, capable of measuring both of the porosity and the permeability in the state that the confining pressure is applied once, and continuously measuring the variation characteristic in the porosity and the permeability of the core sample according to the salt precipitation.

Another object of the present invention is to provide a method for measuring porosity and permeability of a carbon dioxide underground storage medium, capable of measuring the porosity and permeability of the carbon dioxide underground storage medium and the variation in the porosity and permeability according to the salt precipitation by using the apparatus.

In order to accomplish the above object of the present invention, there is provided an apparatus for measuring porosity and permeability of a carbon dioxide underground storage medium. The apparatus includes a holder receiving a core sample acquired from a stratum for carbon dioxide underground storage and blocked at front and rear portions thereof about the core sample, a pressure pump applying a confining pressure to the core sample fixed into the holder, a gas chamber having an inlet linked with a gas storage container to store gas supplied from the gas storage container, and an outlet linked with the holder to supply the stored gas to the core sample received in the holder, a first pressure gauge measuring an internal pressure of the gas chamber, a second pressure gauge measuring an internal pressure of the holder provided at a front of the core sample, a third pressure gauge measuring an internal pressure of the holder provided at a rear of the core sample, and a gas flow meter linked with the holder to measure a flow rate of gas passing through the core sample received in the holder.

In this case, the apparatus may further include an oven for heating the holder such that the core sample is maintained at a predetermined temperature.

In addition, the apparatus may further include a syringe pump having an inlet, which is linked with a liquid-phase carbon dioxide storage container to apply a temperature and a pressure to liquid-phase carbon dioxide supplied from the liquid-phase carbon dioxide storage container such that the liquid-phase carbon dioxide becomes supercritical carbon dioxide, and having an outlet linked with the holder to provide the supercritical carbon dioxide to the core sample received in the holder, and a salt water chamber linked with the holder to provide salt water to the holder such that the core sample is saturated with the salt water.

Further, the apparatus may further include a vacuum pump linked with the salt water chamber to forcibly discharge the salt water and the carbon dioxide of an inner part of the holder such that the inner part of the holder is vacuumized.

In addition, the apparatus further includes a pressure regulator regulating a discharge pressure of the salt water and the carbon dioxide discharged from the holder.

According to another aspect of the present invention, there is provided a method of measuring porosity and permeability of carbon dioxide underground storage medium, which includes (a) applying a confining pressure to a core sample after putting the core sample into a holder, (b) measuring an internal pressure of a gas chamber after filling gas in the gas chamber, (c) calculating the porosity by calculating volume of the gas introduced into the core sample based on variation of the internal pressure of the gas chamber after introducing the gas into the core sample, and (d) calculating a gas permeability coefficient according to Equation 1 in a state that the gas flows through the core sample at a predetermined flow rate, $$K_g = \frac{2\mu Q_b P_b L}{A(P_1^2 - P_2^2)} \times 1000 \qquad \text{Equation 1}$$

In Equation 1, $\mu$: viscosity of the gas, $Q_b$: the flow rate of the gas, $P_b$: atmospheric pressure, $P_1$: pressure at a front of the core sample, $P_2$: pressure at a rear of the core sample, L: a length of the core sample, and A: sectional area of the core sample.

According to still another aspect of the present invention, there is provided a method of measuring porosity and permeability of carbon dioxide underground storage medium, which includes (a) applying a confining pressure to a core sample after putting the core sample into a holder, (b) supplying a salt water stored in a salt water chamber to the core sample such that the core sample is saturated with the salt water, (c) supplying supercritical carbon dioxide to the core sample, (d) vacuumizing an inner part of the holder by discharging the salt water and the supercritical carbon dioxide, (e) measuring an internal pressure of a gas chamber after filling gas in the gas chamber, (f) calculating the porosity by calculating volume of the gas introduced into the core sample based on variation of the internal pressure of the gas chamber after introducing the gas into the core sample, and (g) calculating a gas permeability coefficient according to Equation 1 in a state that the gas flows through the core sample at a predetermined flow rate, $$K_g = \frac{2\mu Q_b P_b L}{A(P_1^2 - P_2^2)} \times 1000 \qquad \text{Equation 1}$$

In Equation 1, $\mu$: viscosity of the gas, $Q_b$: the flow rate of the gas, $P_b$: atmospheric pressure, $P_1$: pressure at a front of the core sample, $P_2$: pressure at a rear of the core sample, L: a length of the core sample, and A: a sectional area of the core sample.

As described above, according to the method and the apparatus for measuring the porosity and permeability of the carbon dioxide underground storage medium of the present invention, the porosity and the permeability of the core sample can be effectively measured in the state that the confining pressure is applied once, so that the core sample can be prevented from denaturalized.

According to the method and the apparatus for measuring the porosity and permeability of the carbon dioxide underground storage medium of the present invention, the variation in the porosity and the permeability caused by the salt precipitation, which occurs in a core according to the injection time or the injected amount of supercritical carbon dioxide, can be continuously measured.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

The advantages, the features, and schemes of achieving the advantages and features will be apparently comprehended by those skilled in the art based on the embodiments, which are detailed later in detail, together with accompanying drawings. The present invention is not limited to the following embodiments but includes various applications and modifications. The embodiments will make the disclosure of the present invention complete, and allow those skilled in the art to completely comprehend the scope of the present invention. The same reference numerals will be assigned to the same elements throughout the whole description.

Hereinafter, an apparatus and a method of measuring the porosity and the permeability of a carbon dioxide underground storage medium according to an exemplary embodiment of the present invention will be described in detail with reference to accompanying drawings.

Figure 1:
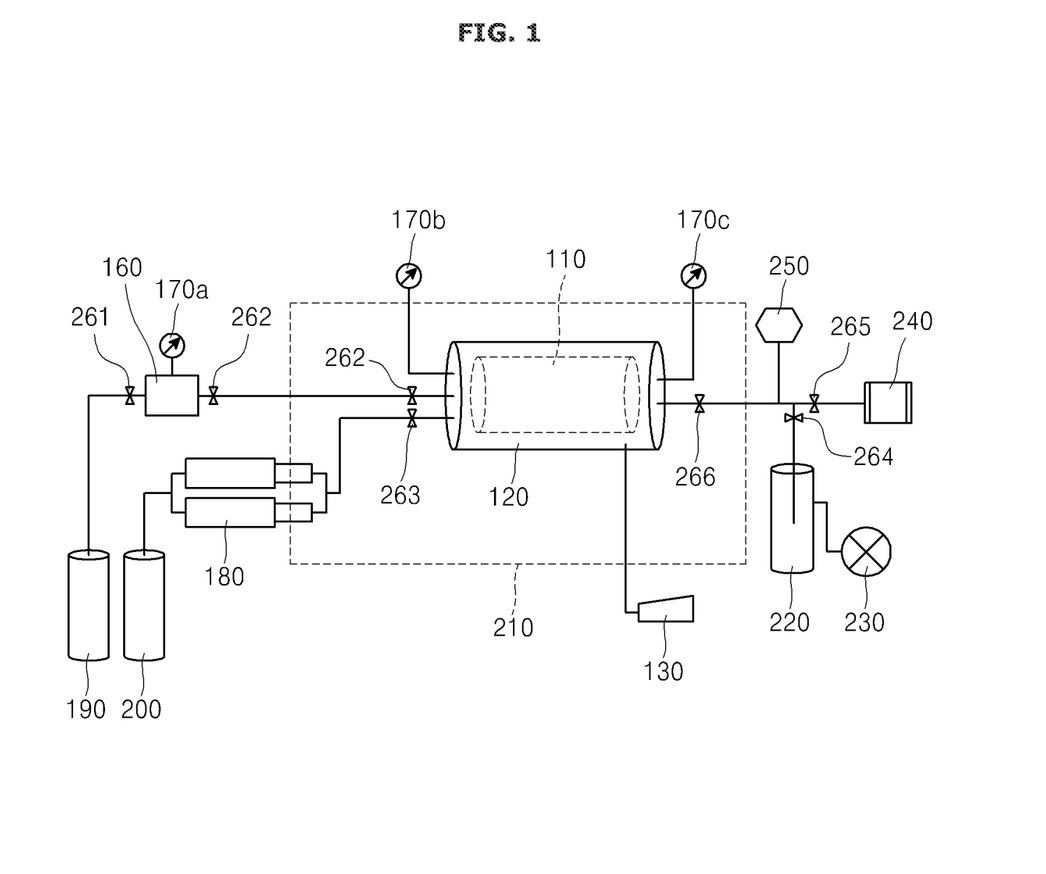
FIG. 1 is a schematic view showing an apparatus for measuring the porosity and the permeability of a carbon dioxide underground storage medium according to the embodiment of the present invention.

FIG. 1 is a schematic view showing an apparatus for measuring the porosity and the permeability of a carbon dioxide underground storage medium according to the embodiment of the present invention.

Referring to FIG. 1, the apparatus for measuring the porosity and the permeability of a carbon dioxide underground storage medium according to the embodiment of the present invention includes a holder 120, a pressure pump 130, a gas chamber 160, first to third pressure gauges 170a, 170b, and 170c, and a gas flow meter 240.

The holder 120 receives a core sample 110.

The core sample 110 is acquired from the stratum for the underground storage of the carbon dioxide, and prepared in such a manner that the core sample 110 is received in the holder 120.

In this case, the inner part of the holder 120 is blocked at the front and rear thereof about the core sample 110. This is because gas is transmitted only through the core sample 110, thereby increasing the accuracy in measuring the porosity and the permeability of the core sample 110.

Meanwhile, the holder 120 is linked with the second and third pressure gauges 17b and 17c. The second pressure gauge 170b measures the internal pressure of the holder 120 provided at the front of the core sample 110. The third pressure gauge 170c measures the internal pressure of the holder 120 provided at the rear of the core sample 110. The second and third pressure gauges 170b and 170c provide pressure variation items required to calculate the permeability of the core sample 110.

The pressure gauge 130 is linked with the holder 120 to apply a confining pressure to the core sample 110 fixed into the holder 120.

The underground storage environment of the carbon dioxide may be simulated by using the pressure pump 130.

An inlet portion of the gas chamber 160 is linked with a gas storage container 190 through a first valve 261 to store gas supplied from the gas storage container 190 as the first valve 261 is opened. In addition, an outlet portion of the gas chamber 160 is linked with the holder 120 through the second valve 262 to supply the gas stored therein to the core sample 110 received in the holder 120 as the second value 262 is open.

The first pressure gauge 170a measures the internal pressure of the gas chamber 160. The first pressure gauge 170a is used to calculate the porosity of the core sample 110.

To this end, the gas chamber 160 may include steel having a predetermined internal volume.

In this case, since the salt precipitated in the pores may be solved in a liquid-phase fluid, the porosity and the permeability coefficient must be measured by using gas. In addition, preferably, the gas includes inert gas. The inert gas prevents undesirable chemical reaction caused by the gas, so that the porosity and the permeability of the core sample 110 can be accurately measured.

The gas flow meter 240 is linked with the holder 120 through a fifth valve 265 to measure the flow rate of the gas passing through the core sample 110 received in the holder 120 as the fifth valve is open.

The gas flow meter 240 provides a gas flow rate item used to calculate the permeability of the core sample 110.

The apparatus for measuring the porosity and the permeability of the carbon dioxide underground storage medium according to the present invention may further include an oven 210 to heat the holder 120.

The oven 210 heats the holder 120 so that the core sample 110 received in the holder 120 is maintained at a preset temperature. Accordingly, the oven 210 may be contributed to simulating the underground environment and may maintain the supercritical carbon dioxide at a supercritical state.

In addition, the apparatus for measuring the porosity and the permeability of the carbon dioxide underground storage medium according to the present invention may further include a syringe pump 180 and a salt water chamber 220. The syringe pump 180 and the salt water chamber 220 are contributed to the measurement of the variation in the porosity and the permeability caused by the salt precipitation occurring as the supercritical carbon dioxide is injected.

An inlet portion of the syringe pump 180 is linked with a liquid-phase carbon dioxide storage container 200 to apply predetermined pressure and predetermined heat to the liquid-phase carbon dioxide supplied from the carbon dioxide storage container 200, so that the liquid-phase carbon dioxide becomes supercritical carbon dioxide. In addition, an outlet portion of the syringe pump 180 is linked with the holder 120 through a third valve 263 to provide the supercritical carbon dioxide to the core sample 110 received in the holder 120 as the third valve 263 is opened.

As shown in FIG. 1, the syringe pump 180 may include dual cylinders in order to inject the supercritical carbon dioxide to the core sample 110 at a constant pressure or at a constant injection rate.

The salt water chamber 220 is linked with the holder 120 through a fourth valve 264, so that the salt water is supplied to the holder 120 as the fourth valve 264 is opened. Accordingly, the core sample 110 may be saturated with salt water.

In this case, a vacuum pump 230 may be linked with the salt water chamber 220. The vacuum pump 230 forcibly discharges the salt water and the carbon dioxide from the holder 120 so that the inner part of the holder 120 becomes in a vacuum state. Although FIG. 1 shows that the vacuum pump 230 is linked with the salt water chamber 220, the present invention is not limited thereto. The vacuum pump 230 may be directly connected to the holder 120.

In addition, the holder 120 may be linked with a pressure regulator 250 through a sixth valve 266. The discharge pressure of the salt water and the carbon dioxide discharged from the holder 129 may be regulated through the pressure regulator 250.

Figure 2:
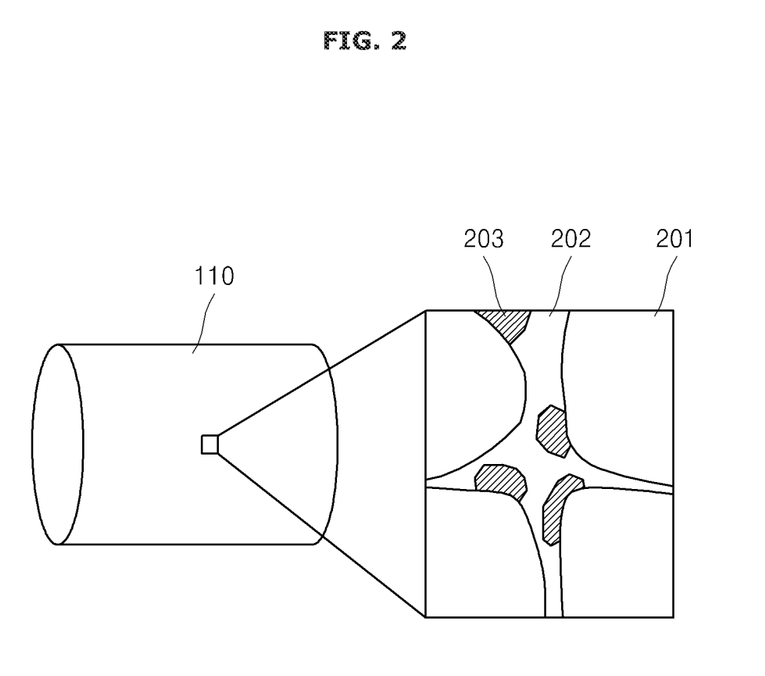
FIG. 2 is a schematic view showing the reduction of a porosity as salt is precipitated in the pores of the core sample according to the evaporation of the salt water by supercritical carbon dioxide when the supercritical carbon dioxide is injected into a core sample saturated with the salt water.

FIG. 2 is a schematic view showing the reduction of the porosity as salt is precipitated in the pores of the core sample according to the evaporation of the salt water by supercritical carbon dioxide when the supercritical carbon dioxide is injected into a core sample saturated with the salt water.

Referring to FIG. 2, a pore 202 exists between mineral particles 201 contained in the core sample 110. In the case of a target stratum for the carbon dioxide underground storage, the pore 202 is generally saturated with salt water. In this case, when the supercritical carbon dioxide is injected, water ($H_2O$) consisting of the salt water is evaporated by the supercritical carbon dioxide, so that the salt may be precipitated. The precipitated salt 203 is filled in the pore 202, thereby exerting an influence on the porosity and the permeability. In other words, if the supercritical carbon dioxide is injected into the salt water, the porosity and the permeability are varied according to the injection time and the injected amount of the supercritical carbon dioxide.

According to the apparatus for measuring the porosity and the permeability of the carbon dioxide underground storage medium of the present invention, through the structure shown in FIG. 1 of the present invention, in the state that the confining pressure is applied once by using one device, both of the porosity and the permeability of the core sample not only can be measured, but the variation in the porosity and the permeability according to the salt precipitation of the underground storage medium can be detected.

Hereinafter, a method of measuring the porosity and the permeability of the carbon dioxide underground storage medium by using the apparatus will be described.

Figure 3:
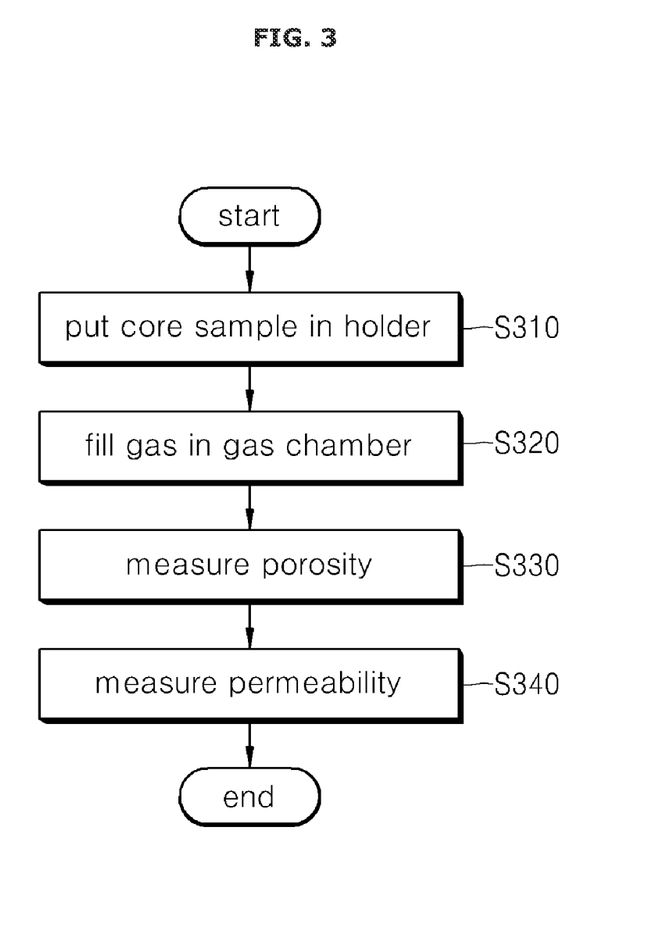
FIG. 3 is a schematic view showing a method of measuring the porosity and the permeability of a carbon dioxide underground storage medium according to the embodiment of the present invention.

FIG. 3 is a schematic view showing the method of measuring the porosity and the permeability of the carbon dioxide underground storage medium according to the embodiment of the present invention.

Referring to FIG. 3, the method of measuring the porosity and the permeability of the carbon dioxide underground storage medium includes a step of seating a core sample (step S310), a step of filling gas in a gas chamber (step S320), a step of measuring the porosity (step S330), and a step of measuring the permeability (step S340).

According to the step of seating the core sample (step S310), after putting a dried core sample into the holder, a confining pressure corresponding to that of an underground storage environment is applied to the core sample by using a pressure pump.

According to the step of filling the gas in the gas chamber (step S320), after filling gas such as nitrogen gas in the gas chamber as a first valve is open, the internal pressure of the gas chamber is measured.

According to the step of measuring the porosity (step S330), after introducing the gas into the core sample as a second valve is open, the volume of the gas introduced into the core sample is calculated based on the variation of the internal pressure of the gas chamber, thereby calculating the porosity.

To this end, the state equation defined as "$P_1V_1=P_2V_2$" may be used. In the state equation, $P_1$ and $V_1$ denote the initial internal pressure of the gas chamber and the volume of the gas chamber, respectively. Further, in the state equation, $P_2$ and $V_2$ represent the internal pressure of the gas chamber after the gas has been introduced into the core sample, and the sum of volumes of spaces of the gas chamber and the holder in which the gas may exist, respectively.

The spaces of the holder in which gas may exist may be the front and rear of the core sample and the internal pores of the core sample. Since the volumes of the gas chamber, the holder, and the front and rear volumes of the core sample can be previously recognized, the volume of the pores with respect to the entire volume of the core sample (i.e., porosity) can be calculated.

In addition, the internal volume of the tube connecting the gas chamber to the holder may be the space in which gas exists. In this case, the internal volume of the tube may be considered to calculate the porosity.

According to the step of measuring the permeability (step S340), a gas permeability coefficient ($K_g$) is calculated through following Equation 1 in the steady state in which gas flows to the gas flow meter through the core sample at a constant flow rate as the fifth and sixth valves are open.

$$K_g = \frac{2\mu Q_b P_b L}{A(P_1^2 - P_2^2)} \times 1000 \qquad \text{Equation 1}$$

In Equation 1, $\mu$: the viscosity of gas, $Q_b$: the flow rate of gas, $P_b$: atmospheric pressure, $P_1$: pressure at the front of the core sample, $P_2$: pressure at the rear of the core sample, L: depth of core sample, A: sectional area of core sample.

Figure 4:
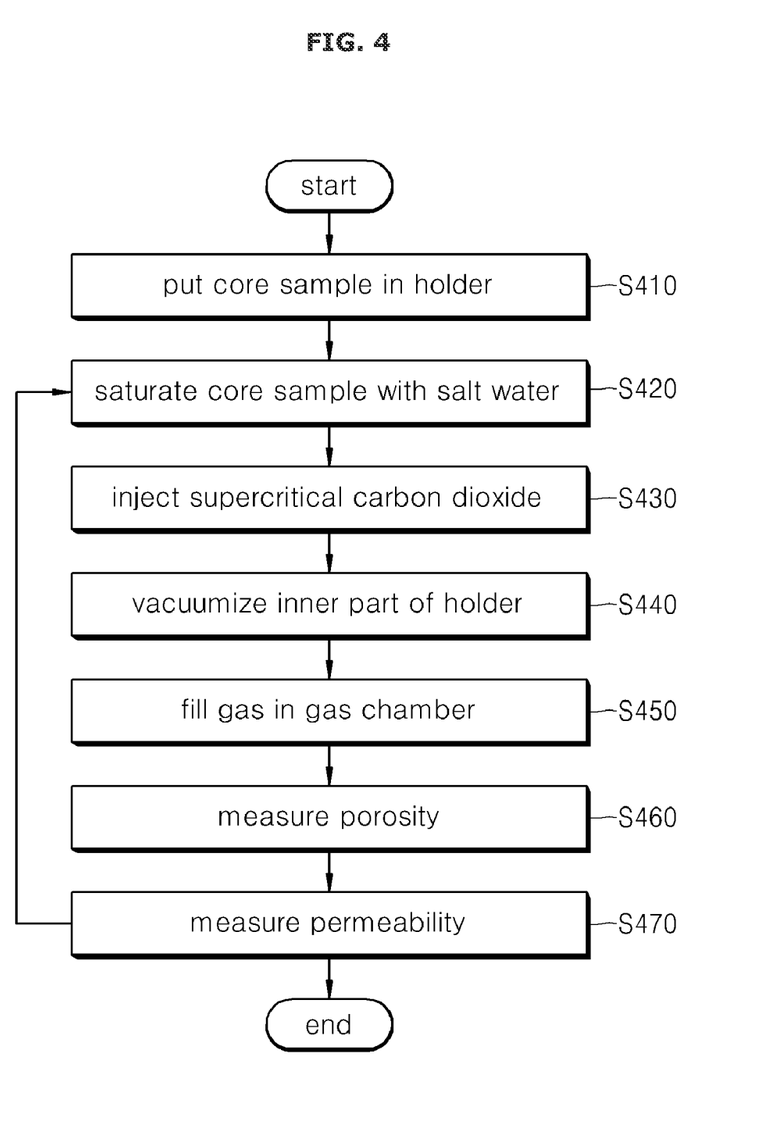
FIG. 4 is a schematic view showing a method of measuring the porosity and the permeability of a carbon dioxide underground storage medium according to another embodiment of the present invention.

FIG. 4 is a schematic view showing a method of measuring the porosity and the permeability of a carbon dioxide underground storage medium according to another embodiment of the present invention.

The method of measuring the porosity and the permeability of the carbon dioxide underground storage medium shown in FIG. 4 is suggested by taking the salt precipitation of the carbon dioxide underground storage medium in the underground storage of the supercritical carbon dioxide into consideration. The method includes a step of seating a core sample (step S410), a step of saturating salt water (step S420), a step of injecting the supercritical carbon dioxide (step S430), a step of vacuumizing the inner part of the holder (step S440), a step of filling gas in the gas chamber (step S450), a step of measuring the porosity (step S460), and a step of measuring the permeability (step S470).

According to the step of seating the core sample (step S410), after seating the core sample in the holder, the confining pressure is applied to the core sample.

According to the step of saturating the salt water (step S420), the state of the core becomes a vacuum state by using the vacuum pump and then the salt water stored in the salt chamber is supplied to the core sample as the fourth valve is opened, so that the core sample is saturated with the salt water.

According to the step of injecting the supercritical carbon dioxide (step S430), the supercritical carbon dioxide is injected into the core sample at a predetermined injection rate as the third valve is open. As the supercritical carbon dioxide is injected to the core sample, the salt water existing in the pore of the core sample is pushed toward the rear of the core sample so that the salt water is moved into the salt water chamber. As a portion of the salt water is evaporated by the supercritical carbon dioxide, the slat is precipitated in the pores.

According to the step of vacuumizing the inner part of the holder (step S440), the salt water and the supercritical carbon dioxide are discharged so that the inner part of the holder is vacuumized. In detail, the inner part of the holder is vacuumized by using the vacuum chamber connected to the salt chamber.

The step of saturating salt water (step S420), the step of injecting the supercritical carbon dioxide (step S430), and the step of vacuumizing the inner part of the holder (step S440) are processes simulating the reduction of pores caused by the salt precipitation in the underground storage medium when the supercritical carbon dioxide is stored under the ground.

Next, according to the step of filling the gas in the gas chamber (step S450), after filling the gas in the gas chamber as the first valve is open, the internal pressure of the gas chamber is measured.

According to the step of measuring the porosity (step S460), after introducing the gas into the core sample as the second valve is open, the volume of the gas introduced into the core sample is calculated based on the variation of the internal pressure of the gas chamber, so that the porosity is calculated.

According to the step of measuring the permeability (step S470), a gas permeability coefficient ($K_g$) is calculated through following Equation 1 in the state in which gas flows to the gas flow meter through the core sample at a constant flow rate as the fifth and sixth valves are open.

The step of filling gas in the gas chamber (step S450), the step of measuring the porosity (step S460), and the step of measuring the permeability (step S470) may be performed in the same manner as that of the steps (steps S320 to S340) of FIG. 3.

After the porosity and the permeability have been calculated through the above procedures, the process steps may be repeated from the step of saturating the salt water (step S420). Therefore, the porosity and the permeability can be calculated until the desirable injection time or the desirable injected amount of the supercritical carbon dioxide comes.

As described above, according to the apparatus and the method of measuring the porosity and the permeability of the carbon dioxide underground storage medium of the present invention, in the state that the confining pressure is applied once, both of the porosity and the permeability of the core sample can be calculated.

Further, according to the apparatus and the method of measuring porosity and permeability of the carbon dioxide underground storage medium of the present invention, the variation in the porosity and the permeability caused by the salt precipitation occurring as the supercritical carbon dioxide is injected into the core sample saturated with the salt can be continuously calculated without the procedure of attaching or detaching the core sample.

Although the present invention has been described by making reference to the embodiments and accompanying drawings, it should be understood that the present invention is not limited to the embodiments but includes all modifications, equivalents and alternatives. Accordingly, those skilled in the art should understand the spirit and scope of the present invention as defined in the following claims. In addition, those skilled in the art should understand that the equivalents and the modifications belong to the scope of the spirit of the present invention.

What is claimed is:

1. An apparatus for measuring porosity and permeability of a carbon dioxide underground storage medium, the apparatus comprising:
  a holder receiving a core sample acquired from a stratum for carbon dioxide underground storage and blocked at front and rear portions thereof about the core sample;
  a pressure pump applying a confining pressure to the core sample fixed into the holder;
  a gas chamber having an inlet linked with a gas storage container to store gas supplied from the gas storage container, and an outlet linked with the holder to supply the stored gas to the core sample received in the holder;
  a first pressure gauge measuring an internal pressure of the gas chamber;
  a second pressure gauge measuring an internal pressure of the holder provided at a front of the core sample;
  a third pressure gauge measuring an internal pressure of the holder provided at a rear of the core sample; and
  a gas flow meter linked with the holder to measure a flow rate of the gas passing through the core sample received in the holder,
    wherein a gas permeability coefficient ($K_g$) is calculated according to Equation 1 in a state that the gas flows through the core sample at a predetermined flow rate, $$K_g = \frac{2\mu Q_b P_b L}{A(P_1^2 - P_2^2)} \times 1000 \qquad \text{Equation 1}$$

in which $\mu$: viscosity of the gas, $Q_b$: the flow rate of the gas, $P_b$: atmospheric pressure, $P_1$: pressure at a front of the core sample, $P_2$: pressure at a rear of the core sample, L: a length of the core sample, and A: sectional area of the core sample.

2. The apparatus of claim 1, further comprising an oven heating the holder such that the core sample is maintained at a predetermined temperature.

3. The apparatus of claim 1, further comprising:
  a syringe pump having an inlet, which is linked with a liquid-phase carbon dioxide storage container to apply a temperature and a pressure to liquid-phase carbon dioxide supplied from the liquid-phase carbon dioxide storage container such that the liquid-phase carbon dioxide becomes supercritical carbon dioxide, and having an outlet linked with the holder to provide the supercritical carbon dioxide to the core sample received in the holder; and
  a salt water chamber linked with the holder to supply salt water to the holder such that the core sample is saturated with the salt water.

4. The apparatus of claim 3, further comprising a vacuum pump linked with the salt water chamber to forcibly discharge the salt water and the carbon dioxide of an inner part of the holder such that the inner part of the holder is vacuumized.

5. The apparatus of claim 4, further comprising a pressure regulator regulating a discharge pressure of the salt water and the carbon dioxide discharged from the holder.

6. The apparatus of claim 1, wherein the gas is inert gas.

7. A method of measuring porosity and permeability of carbon dioxide underground storage medium by using the apparatus claimed according to claim 1, the method comprising:
  (a) applying a confining pressure to a core sample after putting the core sample into a holder;
  (b) measuring an internal pressure of a gas chamber after filling gas in the gas chamber;
  (c) calculating the porosity by calculating volume of the gas introduced into the core sample based on variation of the internal pressure of the gas chamber after introducing the gas into the core sample; and
  (d) calculating a gas permeability coefficient according to Equation 1 in a state that the gas flows through the core sample at a predetermined flow rate, $$K_g = \frac{2\mu Q_b P_b L}{A(P_1^2 - P_2^2)} \times 1000 \qquad \text{Equation 1}$$

in which $\mu$: viscosity of the gas, $Q_b$: the flow rate of the gas, $P_b$: atmospheric pressure, $P_1$: pressure at a front of the core sample, $P_2$: pressure at a rear of the core sample, L: a length of the core sample, and A: sectional area of the core sample.

8. The method of claim 7, wherein the gas is inert gas.

9. A method of measuring porosity and permeability of carbon dioxide underground storage medium by using the apparatus claimed according to claim 3, the method comprising:
  (a) applying a confining pressure to a core sample after putting the core sample into a holder;
  (b) supplying a salt water stored in a salt water chamber to the core sample such that the core sample is saturated with the salt water;
  (c) supplying supercritical carbon dioxide to the core sample;
  (d) vacuumizing an inner part of the holder by discharging the salt water and the supercritical carbon dioxide;
  (e) measuring an internal pressure of a gas chamber after filling gas in the gas chamber;
  (f) calculating the porosity by calculating volume of the gas introduced into the core sample based on variation of the internal pressure of the gas chamber after introducing the gas into the core sample; and
  (g) calculating a gas permeability coefficient according to Equation 1 in a state that the gas flows through the core sample at a predetermined flow rate, $$K_g = \frac{2\mu Q_b P_b L}{A(P_1^2 - P_2^2)} \times 1000 \qquad \text{Equation 1}$$

in which μ: viscosity of the gas, $Q_b$: the flow rate of the gas, $P_b$: atmospheric pressure, $P_1$: pressure at a front of the core sample, $P_2$: pressure at a rear of the core sample, L: a length of the core sample, and A: a sectional area of the core sample.

10. The method of claim 9, wherein the inner part of the holder is vacuumized by using a vacuum pump linked with the salt water chamber.

11. The method of claim 9, wherein steps (b) to (g) are repeated.

12. The method of claim 9, wherein the gas is inert gas.

13. The method of claim 10, wherein the gas is inert gas.

14. The method of claim 11, wherein the gas is inert gas.

* * * * *